(12) United States Patent
Groitzsch et al.

(10) Patent No.: US 7,008,685 B2
(45) Date of Patent: Mar. 7, 2006

(54) LAMINATED MATERIAL AND METHOD FOR ITS PRODUCTION

(75) Inventors: Dieter Groitzsch, Hirschberg (DE); Gerhard Schaut, Hemsbach (DE)

(73) Assignee: Carl Freudenberg KG, Weinheim (DE)

( * ) Notice: Subject to any disclaimer, the term of this patent is extended or adjusted under 35 U.S.C. 154(b) by 0 days.

(21) Appl. No.: 10/157,631

(22) Filed: May 29, 2002

(65) Prior Publication Data

US 2003/0026948 A1 Feb. 6, 2003

(30) Foreign Application Priority Data

May 30, 2001 (DE) ................... 101 26 143

(51) Int. Cl.
*B32B 3/28* (2006.01)
*B32B 3/24* (2006.01)

(52) U.S. Cl. .................. 428/152; 428/138; 428/137; 428/198; 428/110; 428/114; 428/181; 428/179; 428/174; 428/175; 428/182; 428/162; 428/163; 442/36; 442/57

(58) Field of Classification Search ............. 428/152, 428/137, 198, 114, 110, 181, 174, 175, 182, 428/162, 163, 138, 179; 442/36, 57
See application file for complete search history.

(56) References Cited

U.S. PATENT DOCUMENTS

| | | | |
|---|---|---|---|
| 1,331,817 A | 2/1920 | McNab | |
| 3,597,299 A * | 8/1971 | Thomas et al. | 428/108 |
| 3,639,917 A * | 2/1972 | Althouse | 2/270 |
| 4,522,863 A | 6/1985 | Keck et al. | |
| 4,525,407 A * | 6/1985 | Ness | 428/138 |
| 4,606,964 A * | 8/1986 | Wideman | 428/152 |
| 5,611,791 A | 3/1997 | Gorman et al. | |
| 6,462,253 B1 * | 10/2002 | Magnusson et al. | 604/378 |
| 6,491,777 B1 * | 12/2002 | Bevins et al. | 156/167 |

FOREIGN PATENT DOCUMENTS

| | | |
|---|---|---|
| DE | 4 130 343 | 7/2002 |
| EP | 0 137 644 | 4/1985 |
| EP | 0 321 980 | 6/1989 |
| EP | 0 792 629 | 9/1997 |
| EP | 0 814 189 | 12/1997 |
| WO | WO 95/03171 | 2/1995 |
| WO | 98/06290 | 2/1998 |
| WO | WO 98/52458 | 11/1998 |
| WO | WO 00/37003 | 6/2000 |
| WO | WO 00/40793 | 7/2000 |

* cited by examiner

*Primary Examiner*—William P. Watkins, III
(74) *Attorney, Agent, or Firm*—Kenyon & Kenyon

(57) ABSTRACT

A laminate is claimed, having a first cover layer, a fabric with perforations as the middle layer, and a second cover layer, as are a method for its production and the use of the laminate as a fluid absorption and distribution layer made of a nonwoven fabric layer oriented in the Z direction, for absorbent hygiene articles. A three-dimensional form is achieved in that the fabric is present in the shrunk state in the middle layer, i.e. is brought into this state.

23 Claims, 9 Drawing Sheets

LAMINATED MATERIAL AND METHOD FOR ITS PRODUCTION

FIELD OF THE INVENTION

The invention relates to a laminate having a first cover layer, a fabric with perforations as the middle layer, and a second cover layer, as well as to a method for its production, and to the use of the laminate as a fluid absorption and distribution layer made of a nonwoven fabric laminate aligned in the Z direction, for absorbent hygiene products.

BACKGROUND INFORMATION

At present, the absorbent core of baby diapers, incontinence products, and feminine hygiene products is covered on the wearer's side, i.e. on the side facing the body, with at least two layers. An absorption and distribution layer of nonwoven fabric or reticulated foam material is positioned between the cover nonwoven fabric, i.e. the perforated film, and the absorbent core; as the name already indicates, it rapidly absorbs the bodily fluid (urine, thin feces, or menses) and distributes it, as uniformly as possible, to the absorbent core that lies underneath and is usually made up of cellulose and superabsorber powder. In this way, the human skin is kept dry, with the result of preventing skin irritations, on the one hand, and on the other hand, leakage of the bodily fluid caused by an exit to the side is prevented. On the back, the absorbent hygiene product is sealed with a water-proof film or a nonwoven fabric/film laminate, to prevent the bodily fluid from passing through.

For the acquisition and distribution layer, nonwoven fabrics thermally bonded in a hot-air-flow dryer or bonded with polymer dispersions, made of crimped, relatively coarse-titer fibers are known. The fibers have titers of more than 3.3. dtex and are preferably made up of polyesters (polyethylene terephthalate) and/or polyolefins, where for the purpose of fiber bonding in flow-through ovens, bicomponent fibers with a side-by-side or a core/mantle structure are used, and one of the two fiber components melts at a clearly lower temperature than the other component. Such nonwoven fabrics demonstrate a relatively high volume with regard to their low weight, and in particularly, a great thickness, immediately after their production. However, it is known that this initial thickness is already clearly reduced when the goods are rolled up under the tensions usual in practice, and that the compression conditions in the package make a further contribution to reducing the thickness.

Therefore, an attempt was made to find solutions to achieve a thickness not solely by more or less statistically distributed crimped fibers and their bonding, but to bring such crimped fiber nonwoven fabrics into the third dimension, which is described as the Z direction, by way of undulation or other geometric alignment. It has been shown that in this way, greater compression resistance can be achieved than with so-called high-loft nonwoven fabrics, with the result of a clearly lower loss in thickness when passing through the production steps for a diaper, including packaging and storage.

A laminate made up of film and pleated fiber sheet layers is described in WO 92/01401 (U.S. Pat. No. 5,611,791). The laminate is made up of a polypropylene monofilament film and polypropylene fibers that are undulated or aligned in the Z direction in other geometrical structures. The polypropylene fibers are intimately bonded to the polypropylene monofilaments in the valleys of the waves.

The method for the production of such a monofilament nonwoven fabric laminate is described in WO 98/06290. The carded polypropylene staple fiber sheets pass through the nip between two hot, intermeshing positive and negative rollers, are brought into wave shape there, and after leaving the calander roller nip are kept in this shape by blowing on and drawing off hot air, until the waves are finally bonded to the polypropylene fibers of the film, at their raised areas, by being pressed against the polypropylene film between a smooth roller and a corrugated roller. A disadvantage of this method and the resulting undulated laminate is the fact that the wave height in the product is determined exclusively by the wave height of the intermeshing positive and negative calander rollers and that this height is subject to severe limitations.

It is true that such a laminate demonstrates the desired undulation, but it is unsuitable as an acquisition and distribution layer, because the film prevents the bodily fluid from being passed on to the absorbent core.

PRESENTATION OF THE INVENTION

The task of eliminating the aforementioned disadvantages, with regard to both the method and the laminate, and of imparting improved properties for bodily fluid management to the laminate, was accomplished with the invention.

According to the present invention, a laminate is proposed, having a first cover layer, a fabric with perforations as the middle layer, and a second cover layer, where the fabric is present in the shrunk state.

The term fabric is understood to mean a plastic net or interlaid scrim or other flat material that can shrink and is provided with perforations. For the sake of simplicity, the word "net" is used from here on, even though shrinkable interlaid scrims or other fabrics having perforations may be meant. Here, the term interlaid scrim is understood to mean nets whose filaments are bonded to one another at their intersecting locations, using an additional adhesive or binder. The intersecting filaments, i.e. monofilaments or multifilaments, can be made of the same or different polymer material(s), and have the same or different thickness(es). In contrast, the term plastic net defines a net whose intersecting filaments are hot-bonded or bonded to one another with their own polymer mass.

In a particular embodiment of the invention, the fabrics used are ones that possess a very high shrinkage capacity in the machine running direction, and a very low one, or no shrinkage capacity at all, in the crosswise direction. Among other things, nets are known that are either made up of the same thermoplastic, but whose filaments are many times thicker, i.e. heavier in the machine running direction than in the crosswise direction, or nets that are made up of two different polymers, where their filaments are composed of material that can shrink, in the machine running direction, and of material that cannot shrink under process conditions, in the crosswise direction.

This can also happen when the polymers are the same, in that the net is stretched only in the machine running direction, or more in the machine running direction than in the crosswise direction. A higher degree of stretching results in greater shrinkage.

In a particular embodiment, nets with very coarse monofilaments in the lengthwise direction and very fine monofilaments in the crosswise direction, made of the same polymer, such as polypropylene, for example, are used. The process conditions of calandering are selected in such a way that the very fine crosswise filaments of the net melt, and their melt mass collects at the lengthwise filaments. In this special embodiment, a laminate is formed with parallel, defined crosswise undulations on both sides of the shrunk net.

Because the first and the second cover layer are made up of fibers and/or filaments with a melting point at least 30° C. above the melting or softening point of the fabric, only the fabric is responsible for the shrinkage.

It is advantageous if at least one cover layer is made of crimped staple fiber sheets or endless filaments. It is also possible that at least one cover layer is made up of a pre-bonded fabric, for example paper or nonwoven fabric. Because thermoplastically deformable and hot-bondable material is present in at least one cover layer, at least in part, it is possible to hot-bond the laminate for the purpose of connecting the individual layers with one another.

One of the two crimped staple fiber sheets or endless filament layers can be replaced with another already pre-bonded fabric, such as paper or nonwoven fabric. Also in this case, it is true that no fiber component or other component with a melting or softening point below that of the net is used. At least one of the two layers that surround the net must contain thermoplastically deformable and hot-bondable fibers or other components, at least in part. One or both of the layers can contain non-melting, permanently fluid-absorbent fibers, such as cellulose, cotton, wool, lyocell, and the like, at least in part. If one of the two layers does not contain any kind of fibers that can hot-bond by heat and pressure under the process conditions, at least the other layer must contain such a fiber.

The fabric in the middle layer can be an interlaid scrim whose filaments are bonded to one another at the intersection points using an additional adhesive or binder, or a net made of polymer mass, whose intersecting filaments are hot-bonded with one another or bonded to one another with their own polymer mass.

The intersecting straight filaments of the fabric can be arranged at an angle of 90° relative to one another.

It is advantageous if the fabric is formed of material that can shrink under the processing conditions and usage conditions, in one preferential direction, and of material that cannot shrink under these conditions, in a direction perpendicular to the preferential direction.

The fabric can be formed of very coarse, stretched monofilaments in the lengthwise direction and very fine monofilaments in the crosswise direction, made of the same polymer, for example polypropylene. In this case, the melt mass of the melted crosswise filaments can collect on the lengthwise filaments in the laminate.

Another object of the invention is a laminate having a first cover layer, a middle layer made of filaments that do not intersect, and a second cover layer, where the filaments that do not intersect are present in the shrunk state.

It is advantageous if the laminate includes three layers, where the middle layer is made up of parallel monofilaments made of a first thermoplastic, oriented lengthwise, and where monofilaments made of a second thermoplastic are deposited above and/or below the filaments of the first thermoplastic, where the second monofilaments are arranged in such a way that at least two parallel filaments of the first thermoplastic, aligned in a linear orientation, are intersected and bonded.

Instead of a net, lengthwise filaments (strands) that can shrink, or non-intersecting filaments of any form, can be introduced as the middle layer. The monofilaments can be fed in by a warp beam. Preferably, however, they are applied to the lower composite layer, in a parallel arrangement, directly after extrusion, using known methods, before that layer is covered on the top with another layer. It is also possible to achieve an arc-shaped deposition of the monofilaments by pivoting the monofilaments that exit from the die. However, in order to produce a well-defined wave structure of the two outside layers that are raised as a result of shrinkage of the monofilaments, it is advantageous if the arcs of the monofilaments do not intersect. This can be controlled by the distance between the die bores and the arc amplitude.

In this connection, the first monofilaments should have a melting or softening point that is at least 30° higher.

It is advantageous if the second monofilaments are deposited in sine shape over the first monofilaments that are oriented lengthwise.

In this connection, the second monofilaments can have a bicomponent structure, where at least one polymer component has a melting or softening point that is at least 30° higher as compared with the first monofilaments made of a first thermoplastic.

It is advantageous if the shrinkage is 20 to 75% in the lengthwise direction, preferably 30 to 60% with reference to the length of the non-shrunk starting basis.

The laminate can have a mass per unit area of 50 to 200 g/m$^2$, preferably 70 to 150 g/m$^2$, where the second layer makes up 5 to 50%, preferably 10 to 30% of the entire weight.

It is advantageous if the melting or softening point of the fibers of the cover layer is at least 20 to 30° C. above that of the middle layer, i.e. of that part of the middle layer with the lowest melting point, and does not demonstrate any shrinkage, or only an insignificant area shrinkage in comparison with the middle layer.

It is advantageous if the first and/or the second layer are formed of hydrophilic fiber sheets, where preferably there is a hydrophilia gradient between the first and the second cover layer.

Another object of the invention is the use of the laminate for a fluid absorption and/or distribution layer for absorbent hygiene articles.

Finally, a method for the production of a laminate having at least three layers is an object of the invention, where a middle layer in the form of a fabric or in the form of filaments is introduced between two cover layers. According to the invention, in a second step, the fabric or the lengthwise filaments are shrunk at a temperature above the melting or softening temperature of the material of the middle layer, in the roll nip.

To connect the individual layers, at least one roller is engraved with an interrupted pattern, for example dots.

It is advantageous if the three layers are passed to a calander with at least one heated, engraved steel roller, and are connected to form a laminate there, where the connection process can be particularly described as riveting.

In the calander nip, the crosswise filaments can be melted through, cut, or severely damaged.

Furthermore, the filaments can be deposited in arc shape onto the first cover layer, where the filaments are preferably deposited free of intersections with each other.

BRIEF DESCRIPTION OF THE DRAWINGS

The drawings show a laminate according to the invention, and the method according to the invention. These show.

EXPLANATION OF THE INVENTION

Figure 1:
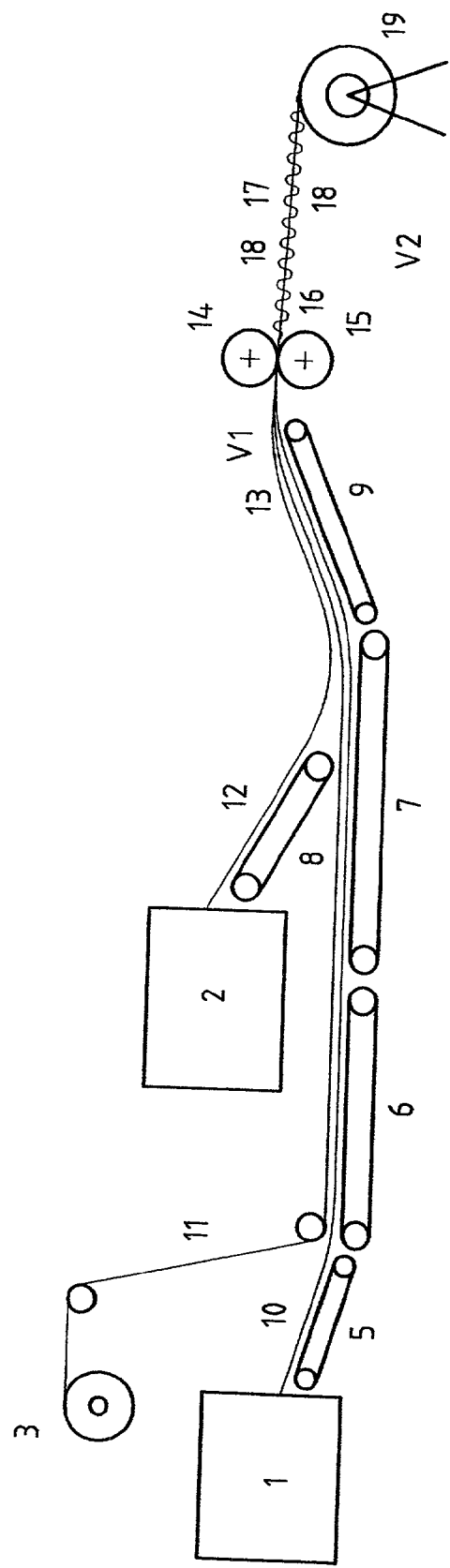
FIG. 1 the method for the production of a shrunk laminate,
FIG. 2 a laminate according to the invention, with a fabric shrunk exclusively in the lengthwise direction, FIG. 3 a detail from FIG. 2, on a larger scale, FIG. 4 a lengthwise cross-section from FIG. 2, along line A—A, FIG. 5 a lengthwise cross-section from FIG. 2, along line B—B, FIG. 6 a cross-section from FIG. 2, along line C—C, FIG. 7 a laminate with a compressed staple fiber nonwoven fabric or a spun nonwoven fabric, with an approximately rectangular cross-section, FIG. 8 a comparison with a non-bundled nonwoven fabric, and FIG. 9 the introduction of the compressed nonwoven fabric strips from FIG. 7 into the laminate.

FIG. 1 schematically shows the method for the production of a shrunk laminate, made up of a first staple fiber sheet, a net, and a second staple fiber sheet.

From a carding machine 1, a loose first fiber sheet 10 of crimped fibers is laid on conveyor belt 5, either in the machine direction or crosswise to the machine direction, or in a random laid layer, and transported on to conveyor belts 6, 7, and 9, which follow conveyor belt 5. A fabric 11 that is guided by a roller 3, by way of deflection rollers, is deposited on this loose first fiber sheet 10, and forms the middle layer. The fabric has perforations and can be structured as a net or as an interlaid scrim. This fabric 11 is finally covered with a second fiber sheet 12, coming from a carding machine 2 via conveyor belt 8.

This three-layer, completely unbonded laminate 13, supported by conveyor belts 7 and 9, finally passes through a roll nip 16 (nip or calander nip) that is delimited by two hot calander rollers 14 and 15. Calander roller 15 is an engraved roller with an interrupted pattern (such as dots, for example), and calander roller 14 is a smooth steel roller.

The temperatures of the two rollers 14 and 15 are set to approximately the same level, in a normal case, if both sheets 10, 12 are made up of fibers with the same melting or softening point. However, at least one of the two roller temperatures must lie at least 20–30° C. above the melting temperature of fabric 11. Upon departure from roll nip 16, spot-bonded laminate 17, simultaneously shrunk in the machine direction, with wave-shaped elevations 18 that extend alternately on both sides of the center plane of fabric 11, is formed.

Between the beginning or end of conveyor belt 9 and the exit from calander nip 16, a width adjusting holder, for example a stretching frame, can additionally be installed, in order to prevent shrinkage in the crosswise direction. This width adjusting holder is not shown in FIG. 1.

Fiber sheets 10, 12 that surround the net are made up of 100% fibers that have a melting or softening point that is clearly, i.e. at least approximately 30° C., above that of the component of fabric 11, which is responsible for the thermal shrinkage.

The wind-up speed $V_2$ at a roll-up device 19 arranged after calander rollers 14, 15 is reduced by the lengthwise shrinkage amount of the fabric as compared with $V_1$ ahead of the calander. If $V_1$ is 100 m/min, for example, and the lengthwise shrinkage is 50%, the roll-up speed $V_2$ is reduced to 50 m/min. It can be appropriate to install a goods storage unit between calander rollers 14 and 15 and roll-up device 19, in order to ensure that the goods are rolled up with as little tension as possible.

Carding machine 1 for laying staple fiber sheet 10 can be replaced by an extruder, a spinneret arrangement, and a directed air stream for the purpose of filament quenching and stretching to form an endless filament nonwoven fabric (spun nonwoven fabric) according to known methods, where the die bores permit spinning of monofilaments or, preferably, bicomponent fibers with a core/mantle structure, or, particularly preferably, with a side-by-side structure, which are known to trigger a desired spiral curl as early as the quenching process. The die bores and air stretching are selected in such a way that relatively large-titer filaments at more than approximately 10 dtex are formed.

In another embodiment of the method, loose fiber sheet 10 made up of staple fibers or random-laid endless filaments can be replaced with a nonwoven fabric that has already been pre-bonded. In this case, as well, coarse fibers are advantageous for the product.

In roll nip 16 of engraved calander roller 14 and smooth calander roller 15, the two nonwoven fabric layers 10 and 12 are spot-bonded or bonded in an interrupted pattern. The likelihood that calander bonding spots will also include fabric 11 is extremely slight.

The fabric can be replaced by monofilaments oriented in the lengthwise direction, which are oriented parallel to one another and can be laid at a uniform distance from one another. The filaments can be wound up on a warp beam and are laid onto lower fiber sheet 10 from there, always at a uniform distance from one another. Loose lower fiber sheet 10 can also be replaced with a nonwoven fabric that has already been pre-bonded. However, the monofilaments can also be extruded onto the lower nonwoven fabric layer directly from the polymer melt.

It is also possible to lay monofilaments made of a second thermoplastic above and below the filaments of the first thermoplastic, from a second extruder and a second die plate, in addition to the parallel monofilaments made of a first thermoplastic and oriented lengthwise, where the die beam from which the monofilaments of the second thermoplastic exit is subjected to an oscillating lateral movement. The oscillation amplitude of the lateral oscillation is selected in such a way that at the exit site, a filament of the second thermoplastic that is laid in sine shape intersects with and bonds at least two parallel filaments of the first thermoplastic with a linear orientation.

The first thermoplastic monofilaments have a melting or softening point that is higher by at least 30° C. The first thermoplastic can be made up, for example, of polypropylene with a melting point of approximately 165° C., and the second of polyethylene terephthalate with a melting point of approximately 260° C. The second filaments, deposited in sine shape by oscillation, can also have a bicomponent structure, such as a side-by-side or core/mantle structure. In this case, at least one polymer component has a melting or softening point that is at least 30° C. higher than the first thermoplastic of the monofilaments with a parallel orientation.

The calander temperature for bonding and, at the same time, shrinkage of the laminate is selected in such a way that exclusively the parallel filaments made of the first thermoplastic are subjected to shrinkage in the lengthwise direction at the exit nip. The corrugation of the laminate that is achieved in this way is a particularly preferred structure of the elevations in the Z direction, which imparts a particularly high level of stability to pressure stress, or pressure and temperature stress, to the product according to the invention.

Such an exclusive shrinkage in the lengthwise direction can also be achieved with a net, if the method according to the invention is modified by a very particular selection of the engraving of the calander roller, in such a way that the crosswise filaments are melted through, cut, or very severely damaged in calander nip 17. For this purpose, the calander roller can have interrupted lengthwise grooves, for example, with an extremely low top groove diameter, thereby increasing the cutting or separation effect. These interrupted lengthwise grooves or rods can be the sole structure element of the engraved roller. This geometric arrangement of the engraving for the main purpose of cutting the crosswise threads can also be combined with engravings that mainly contribute to the bonding strength of the laminate. When using such special rollers that cut the crosswise filaments, fiber sheets with a lengthwise orientation are preferred, where at least one of the two should be a lengthwise sheet.

Figure 2:
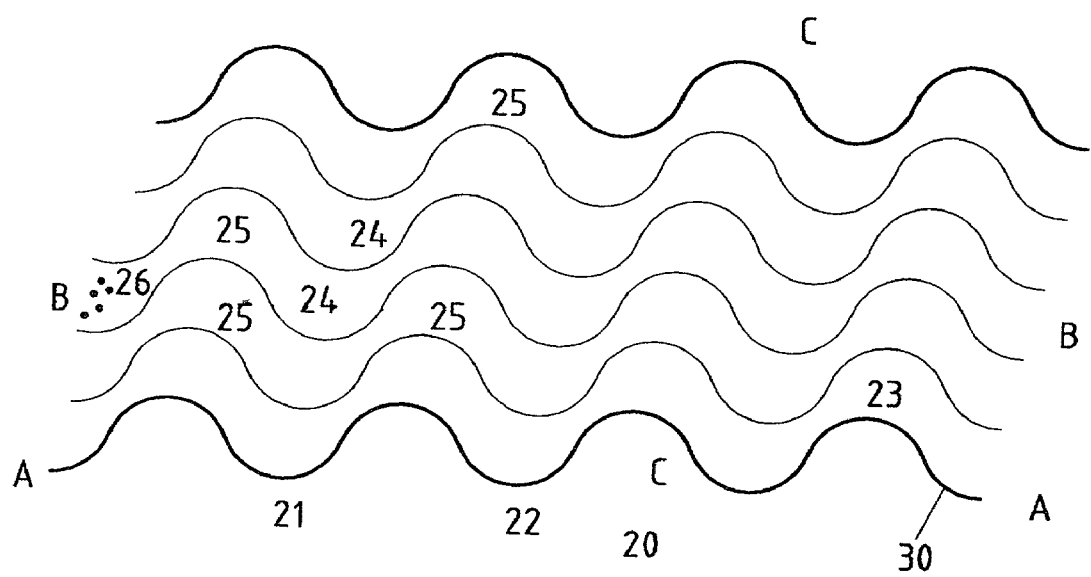

FIG. 2 shows a laminate 20 according to the invention, with a fabric shrunk exclusively in the lengthwise direction. The lengthwise direction of the fabric extends from A to A, i.e. from B to B, the crosswise direction from C to C. The surface of the shrunk laminate is wave-shaped in the lengthwise direction, and includes wave valleys 21, 22 and wave peaks 23. Laminate 20 is reinforced with parallel monofilaments 30, in a region 25. There is a region 24 between monofilaments 30, in which hot-bonding spots 26 are arranged.

Figure 3:
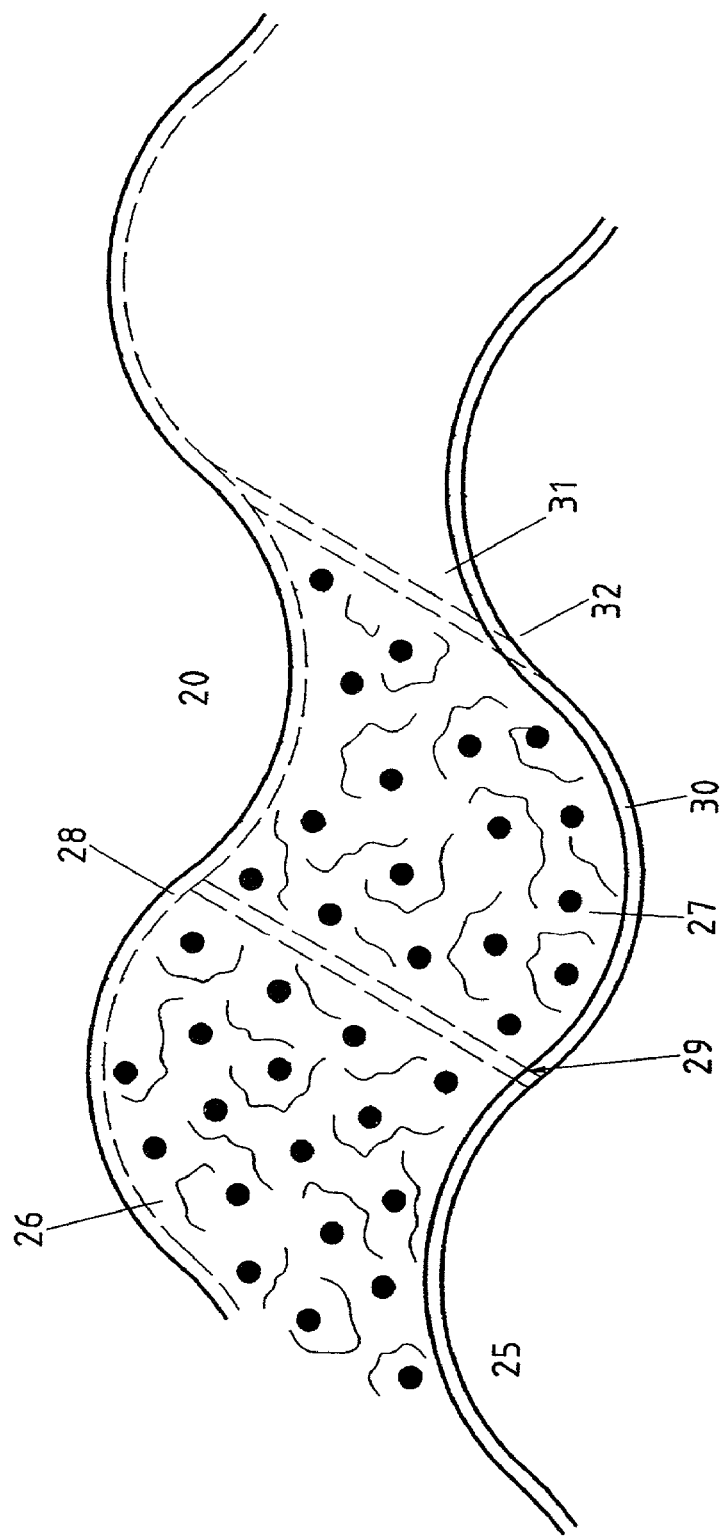

FIG. 3 shows an enlarged detail from FIG. 2. In the areas, i.e. spaces 24 between monofilaments 30, there is an upper layer and a lower layer 31, 32 made of fibers 27, which are bonded together by hot-bonding spots 26. At the turning point of the sine-shaped undulations, in each instance, a crosswise filament 28 is embedded between the two nonwoven fabric layers 31, 32, in each instance, which intersects with lengthwise filament 30 of the fabric at location 29, and is hot-bonded to it. In the zones between hot-bonding spots 26, fibers 27 are generally not bonded. However, in a special embodiment, they can also be cohesively bonded by a binder.

Shrunken lengthwise filament 30 is located in the center of laminate 20. Crosswise filaments 28 are not shrunk, so that laminate 20 has the same width ahead of and after the calander nip.

Figure 4:
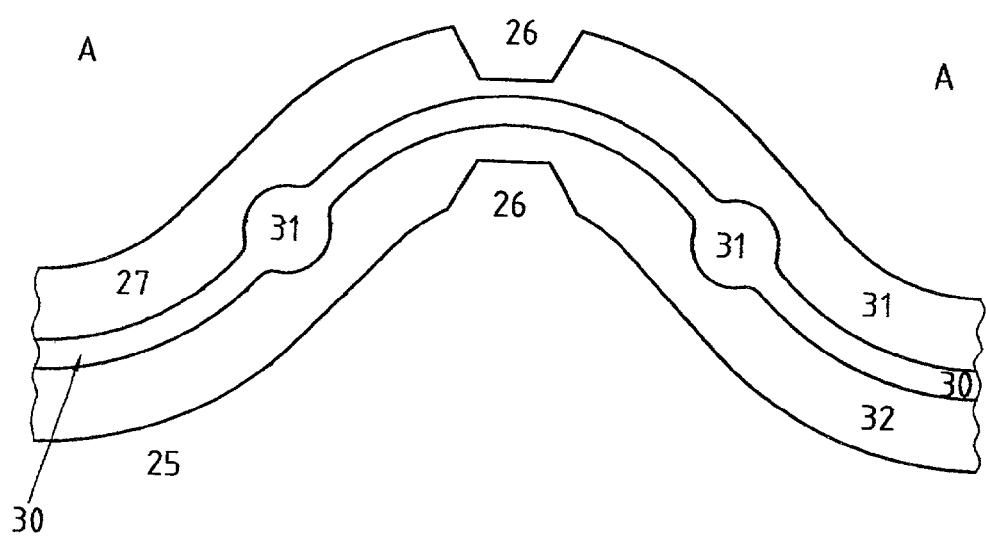

FIG. 4 shows a lengthwise cross-section of FIG. 2 along line A—A. In the middle of the laminate, there is shrunk lengthwise filament 30 of a plastic net. At intersection point 29 (see FIG. 3) of lengthwise and crosswise filaments 30, 28 of the net that are hot-bonded together, a thickened region 31 is shown. At hot-bonding spots 26, fibers 27 of the two nonwoven fabric layers are compressed and bonded to one another. Since hot-bonding spots 26 are arranged in a different spacial plane from that of the lengthwise cross-section shown, the edge contours of the hot-bonding spots are shown with broken lines.

Figure 5:
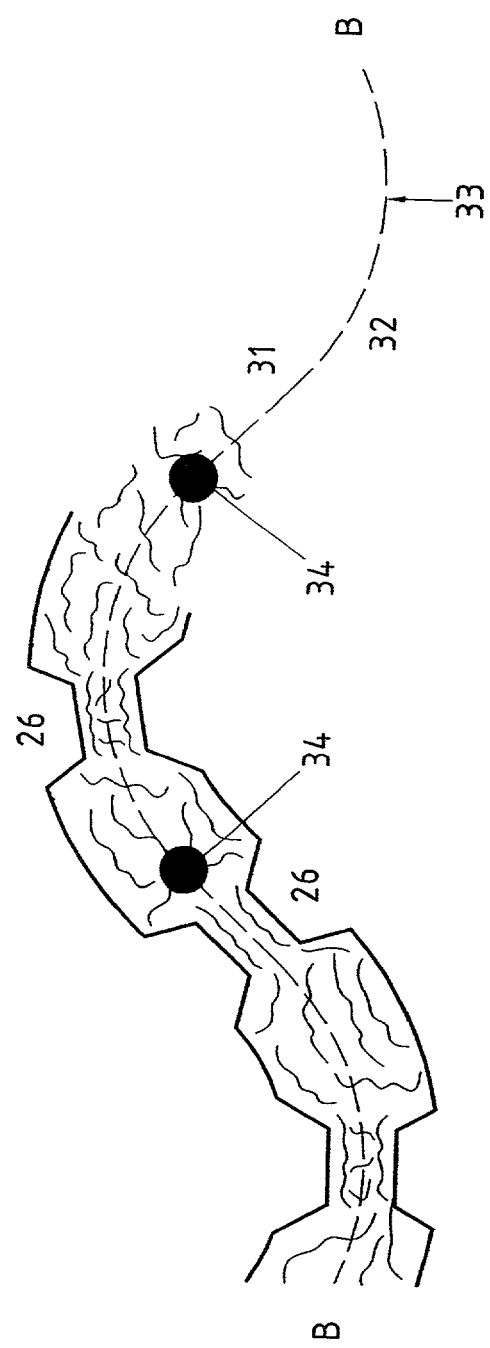

FIG. 5 shows a lengthwise cross-section of FIG. 2 along line B—B, i.e. in a region between lengthwise filaments 30 of the net. Crosswise filaments 28 of the plastic net are shown as cross-section 34 here, the progression of the lengthwise threads is indicated as 33.

Fiber layers 31 and 32 can be qualitatively and quantitatively the same or different. They can be made up of thermoplastic synthetic fibers or blends of such fibers with non-melting hydrophilic fibers such as cellulose, lyocell, cotton, flax, etc., and/or wool.

Thermoplastic fibers that can be bonded with a calander must be contained in at least one of the two nonwoven fabric layers 31 or 32 by at least 20%, in order to ensure sufficient laminate adhesion after calandering.

For the polymer material of lengthwise filament 30, which is arranged in the net as necessary, there is only one restriction, that it has a melting or softening point of at least 30° C. below that of the thermoplastic fiber of layers 31 and/or 32, resulting in the laminate adhesion of the two layers as a result of embossing calandering.

The lengthwise filaments in and of themselves or in the net or lattice can be made up of polyolefins, such as polyethylene and polypropylene, copolymerizates such as ethylene and propylene, of polyamide 6, of copolyamides, copolyesters, etc., or also of thermoplastic elastomers. Their distance from the next adjacent lengthwise filament, in the shrunk state and the non-shrunk state, is at least 2 mm and at most 15 mm. The titer of the lengthwise filaments ranges from 80 to 2,000 dtex, preferably approximately 100 to 1,000 dtex.

The shrinkage in the lengthwise direction is 20 to 75%, preferably 30 to 60% with reference to the length of the non-shrunk starting basis.

The titer of the crimped fibers 27 of layers 31 and 32 of the laminate, which can be bonded by temperature and pressure, ranges from 6.7 to 50 dtex, preferably 15 to 25 dtex. At least a 50% proportion with reference to the total of the fiber weights of layers 31, 21 is made up of crimped fibers with a high level of springiness, such as polyethylene terephthalate or polypropylene, for example.

Figure 6:
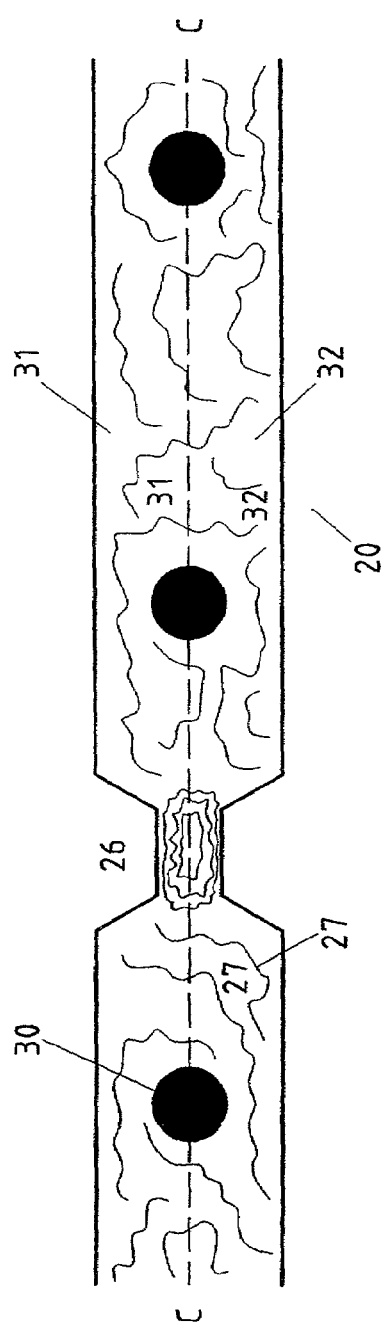

FIG. 6 shows the cross-section of laminate 20 along line C—C. Monofilaments 30 are surrounded by the two fiber layers 31 and 32. Fibers 27 of the two layers 31 and 32 are highly compressed and bonded to one another at hot-bonding spots 26.

Instead of filaments with a circular cross-section, those with any desired cross-section can also be used, such as oval, rectangular, rectangular with rounded-off corners, triangular (trilobal) or also multilobal, for example.

Figure 7:
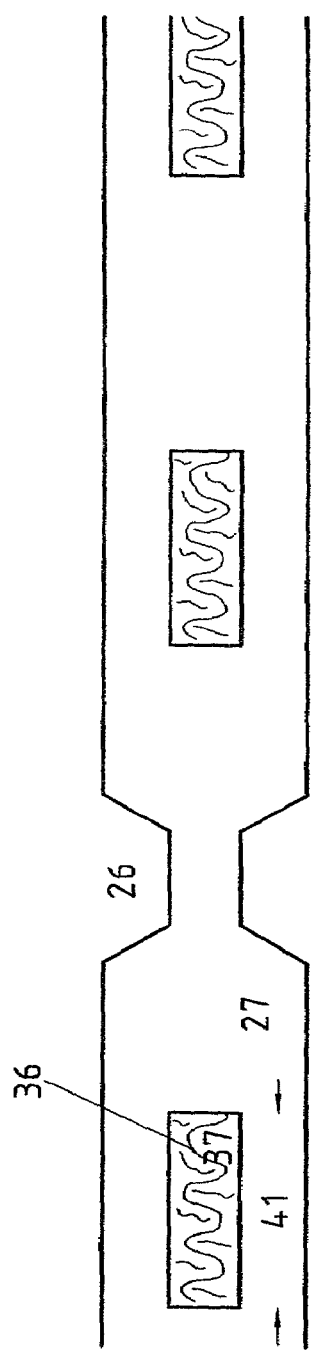
Figure 8:
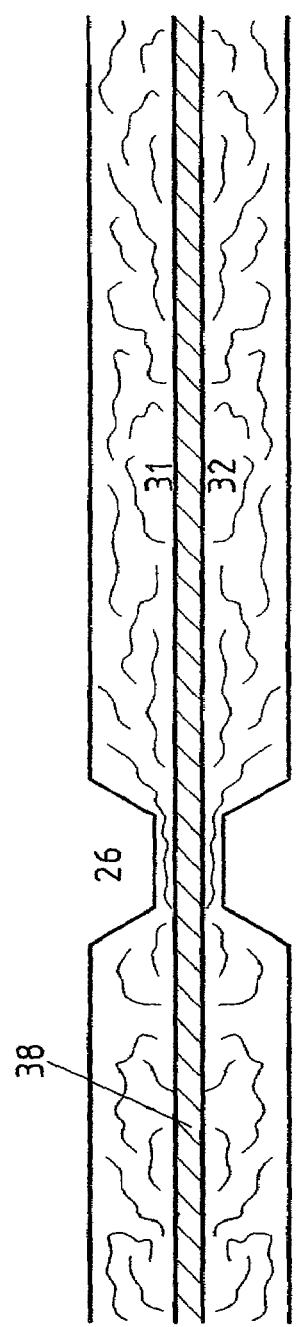
Figure 9:
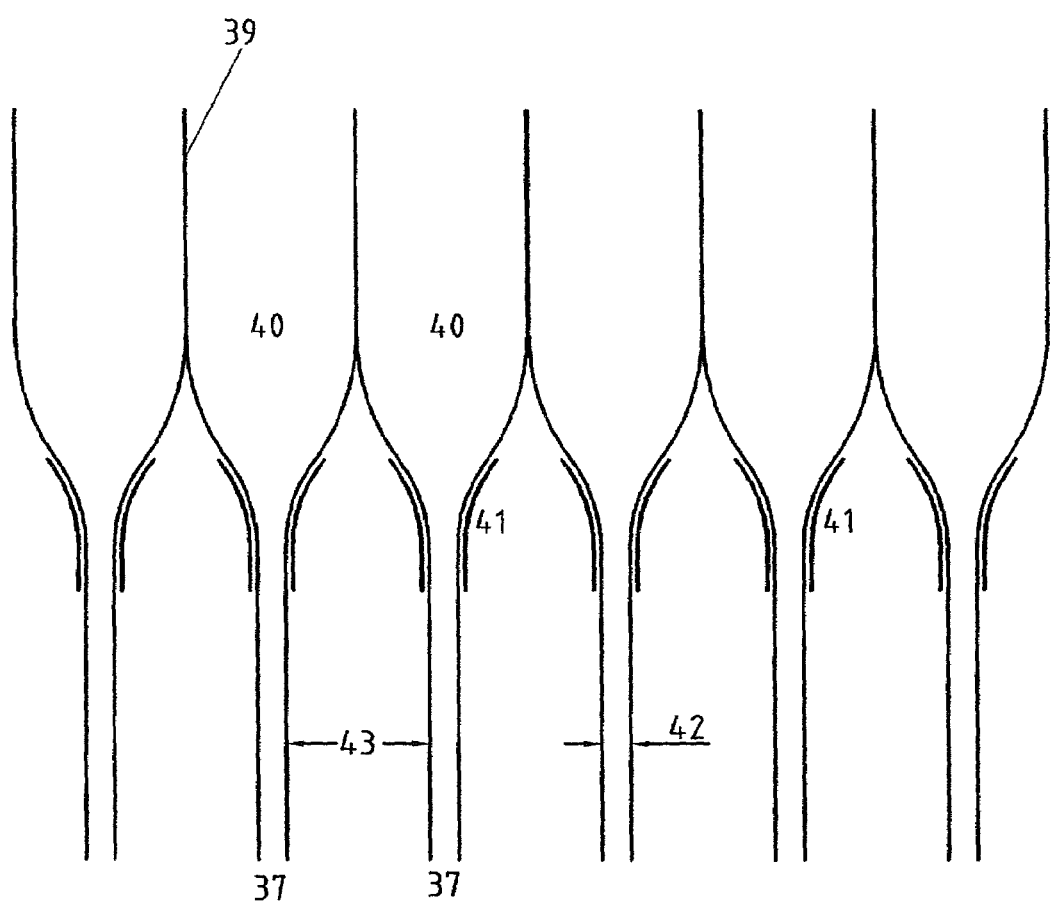

In FIG. 7, monofilaments 30 of FIG. 6 have been replaced with compressed staple fiber nonwoven fabric or spun nonwoven fabric 37, with an approximately rectangular cross-section. FIG. 9 shows how these compressed nonwoven fabric strips 37 were introduced into laminate 20. A light staple fiber sheet 38, with a weight of approximately 6–10 g/m$^2$, combed in the lengthwise direction, is cut into narrow staple fiber sheets 40 of equal width, at locations 39, using a cut sheet mechanism. These are subsequently brought together, for example by weak lateral air streams, to form a very narrow sheet 37 with a width 42, passed through a highly polished tube 41, and finally laid down at uniform distances 43 from one another on the lower carrier sheet, i.e. the lightly pre-bonded nonwoven fabric. Because of the bundling to form a thick fiber sheet 37, the shrinkage force as compared with the non-bundled nonwoven fabric and the wave height, as compared with the case shown in FIG. 8, are clearly increased. Here, a lengthwise sheet 38, i.e. without bundling, was laid between the two fiber sheets 31 and 32, as the shrinking fabric.

The product has a weight of 50 to 200 g/m$^2$, preferably 70 to 150 g/m$^2$, where the middle layer used as the shrinkage medium makes up a proportion of 5 to 50%, preferably 10 to 30%, with reference to the total weight of the laminate, independent of whether only parts of it shrink.

Any known synthetic monofil fibers can be used as staple fibers, as long as they have a softening or melting point that lies at least 20–30° C. above that of the middle layer, i.e. of that part of the middle layer with the lowest melting point, and themselves result in either no area shrinkage or only insignificant area shrinkage, in comparison with the middle layer, under the calander conditions. Also, synthetic bicomponent or multicomponent fibers can be used, where in this case, the above melting/softening and shrinkage restrictions apply to the core that has the higher melting/softening point.

Also unstretched or partially stretched fibers, such as unstretched polyethylene terephthalate fibers, for example, can be used, particularly for bonding purposes, if, for example, the embossing calander bonding temperature of the fully stretched fiber is so great that the shrinkage becomes too great or uncontrollable in the calander nip. Also, blends of unstretched or partially stretched fibers with fully stretched fibers can be recommended.

The two same or different fiber sheets are hydrophilic, i.e. they demonstrate an absorption force for aqueous fluids. Fibers made of polymers that are hydrophobic, in and of themselves, can be given an absorption force for aqueous fluids by adding surfactants or detergents into the polymer melt mass, or these can be applied, from the outside, to the fibers or to the acquisition and distribution layer. Those preparations that impart a permanent wetting property to the product are preferred. For the purpose of permanent hydrophilia, however, it is also possible to blend hydrophobic fibers with regenerated cellulose fibers, such as viscose staple fiber, lyocell, cotton, flax, wool, and the like. The invention also includes an acquisition and distribution layer in which a hydrophilia gradient prevails from layer 31, with a lower hydrophilia, in the direction of layer 32, with a higher hydrophilia.

This can be achieved, for example, in that the percentage proportion of the hydrophilic layers in layer 32 is selected to be higher than in layer 31.

The method proceeds as follows: A plastic net, interlaid scrim that can shrink, or another fabric that can shrink, provided with perforations, is laid between two fiber sheets with the same or different weight, the same or different orientation and composition, and passed to a calander for bonding of the three-layer laminate.

The angle of the intersecting, straight filaments of the net can be >0 to 90°, where in the case of angles not equal to 90°, the intersecting filaments result in 2×angles<90° and 2 angles at 180° minus the amount of the angle<90°, since it is known that the total of the four angles at the intersection points must always total 360°.

In a preferred embodiment, the angle of the intersecting filaments of the net is 4×90°. The straight filaments that are oriented in one direction are always arranged parallel to one another, and the angles of the intersecting filaments are the same, distributed over the entire net area. The distances between the parallel filament pairs can be the same or different. Preferably, ones with equal parallel distances are used.

Aside from being straight, the intersecting filaments can also have a curved or other shape. The geometric shape can repeat over the filament length, at regular or irregular intervals. The curved or other geometric lines of the filaments can be so strongly defined that they overlap or intersect with those of the adjacent filaments with the same orientation.

Any desired arrangement of polymer material that can shrink, in filaments and in a different shape, and alternating with perforations, can be used for the invention.

The net can have thicker filaments in a preferential direction or be made up of filaments that demonstrate a higher shrinkage force in one direction than the other. For cost reasons, nets made of polyolefins are preferably used, and those made of polypropylene are particularly preferably used.

The three layers, which are at first not bonded to one another, are passed to a calander that is made up of a heated, engraved roller and a smooth steel roller, and are riveted to form a composite, by passing through the calander. Immediately after leaving the calander nip, the goods undergo area shrinkage, i.e. shrinkage both in the lengthwise direction and the crosswise direction. Using technical means known to a person skilled in the art, such as temperature control, i.e. temperature reduction, and/or a width adjusting hold, using a stretching frame, severe crosswise shrinkage is prevented at the edges of the goods. This results in goods with elevations, the shape and height of which depend on the design of the net and the shrinkage conditions.

It was surprising that the extremely low dwell time in the calander nip is already sufficient to produce the shrinkage.

EXAMPLE

A biaxially stretched plastic net based on polypropylene, with a weight of 11 $g/m^2$ and a mesh size of 5.0×5.0 mm, is laid between two cross-laid loose staple fiber sheets with a weight of 20 $g/m^2$ each. The two staple fiber sheets are made up of 100% crimped polyethylene terephthalate fibers with a titer of 6.7 dtex and a cut length of 60 mm. The three layers are passed to spot-bonding by calandering between a smooth and an engraved steel roller. The bonding area of the engraved roller is 9.6% and the engraving depth is 0.73 mm. Calandering took place at a temperature of 198° C. on both rollers, and a line pressure of 30 kp/cm at a speed of 10 m/min. The width of the goods before shrinkage was 110 cm. Immediately after departure from the calander nip, wave-shaped elevations formed in the goods, extending almost over the entire width of the goods perpendicular to the machine direction. Only in an edge region with a width of approximately 7 cm, on both sides, there were elevations in the shape of mountain peaks, up and down, and an out-of-proportion weight increase. This edge region is cut off because of its lack of weight constancy and the different type of structure, and it is not used as an absorption and distribution layer. The width of the goods after passing through the calander was reduced from 110 to 92 cm. By cutting off the edge that cannot be used, 2× approximately 7 cm, the useful width was reduced to 78 cm. In this region, there was an area shrinkage in the lengthwise direction of 55.1% after calander passage. The starting weight of 51.0 $g/m^2$, namely 2×20 $g/m^2$ for the staple fiber sheets and 11 $g/m^2$ for the plastic net, was increased, so that the composite weight was 114 $g/m^2$.

The tests were carried out within the useful width of 78 cm. The laminate weight was determined in $g/m^2$, the thickness was determined in mm at a contact pressure of 8 $g/cm^2$. In addition, the thickness was determined at 64 $g/m^2$, for a calculation of the compression resistance KW.

The value for KW is obtained in % by dividing the thickness at 8 $g/cm^2$ by the thickness at 64 $g/m^2$, and multiplying by 100.

To determine the repetition capacity W, the method of procedure is as follows: The thickness D1 is measured at a load of 8 $g/cm^2$, after 30 seconds. Afterwards, the load is increased to 64 $g/cm^2$, by adding a corresponding weight, using the same test element and at exactly the same test location, and the thickness is determined again after 30 seconds of load time. Subsequently, this additional weight is removed again, so that once again, a pressure of 8 $g/cm^2$ rests on the same test element at exactly the same test location. After a load time of another 30 seconds, the thickness in mm is measured again (D2). The repetition capacity W in % is calculated by dividing D2 by D1 and multiplying by 100.

We understand the term creep resistance KB to mean the remaining thickness in % after a permanent load of 35.4 g/m² on the goods, stored in a drying cabinet at 60° C. for a period of 24 hours, in comparison with the thickness of the sample measured at a load of 8 g/m² after 30 seconds.

In detail, the determination of the KB takes place as described in the following lines: 5 test samples with a format of 90×90 mm were cut out. Using these test samples, the thickness at 8 g/cm² load is measured after 30 seconds. Subsequently, the samples are stressed with a round cylinder with a weight of 1 kg and a diameter of 60 mm (corresponds to 3500 Pa=35.4 g/cm²) and stored in the drying cabinet at 60° C. for a period of 24 hours. After the weight is removed, the samples are taken out of the drying cabinet and remain in the unstressed state for 2 minutes. Subsequently, the thickness of the samples is measured under a load of 8 g/cm². The thickness after 24 hours of load at 60° C., divided by the starting thickness, measured at 8 g/cm², in each instance, multiplied by 100, yields KW [sic; KB] in %.

What is claimed is:

1. A laminate material comprising a first cover layer, a middle layer of fabric having perforations thereon, and a second cover layer,
   wherein the fabric has been shrunk to cause alignment in the Z direction of the entire laminate material by way of undulation or other geometric alignment of the fabric, and
   wherein the fabric is formed of a polymer having a relatively coarse monofilaments in the lengthwise direction and a relatively fine monofilaments in the crosswise direction.

2. The laminate material according to claim 1, wherein each of the first and the second cover layer is made up of fibers and/or filaments having a melting point at least 30° C. above the melting or softening point of the fabric.

3. The laminate material according to claim 1, wherein at least one cover layer is made up of crimped staple fiber sheet or continuous filaments.

4. The laminate material according to claim 1, wherein at least one cover layer is made up of a pre-bonded fabric.

5. The laminate material according to claim 1, wherein at least one of the first and second cover layers further comprises thermoplastically deformable and hot-bondable material.

6. The laminate material according to claim 1, wherein the fabric in the middle layer is an interlaid scrim having filaments bonded to one another at their intersecting locations, using an additional adhesive or a binder.

7. The laminate material according to claim 1, wherein the fabric is formed by a net of polymer mass having intersecting filaments that are hot-bonded or bonded to each other by their polymer mass.

8. The laminate material according to claim 1, wherein the fabric is formed by a net of polymer mass having intersecting filaments that are arranged at an angle of 90° relative to one another.

9. The laminate material according to claim 1, wherein the fabric is adapted to shrink under the processing conditions and usage in a preferential direction, and not shrink in a direction perpendicular to the preferential direction.

10. The laminate material according to claim 1, wherein a melt mass of the melted crosswise filaments is collected on the lengthwise filaments.

11. The laminate according claim 1, wherein the shrinkage in the lengthwise direction is 20 to 75% of the length of the non-shrunken starting material.

12. The laminate according claim 1, wherein the laminate has a mass per unit area of 50 to 200 g/m².

13. The laminate according to claim 1, wherein the melting or softening point of the fibers of the first cover layer is at least 20 to 30° C. higher than the melting or softening point of a part of the middle layer with the lowest melting point.

14. The laminate according to claim 1, wherein each of the first and/or the second layer are formed of hydrophilic fiber sheets.

15. The laminate according claim 14, wherein the second layer constitutes 5 to 50% of the entire weight of the laminate.

16. The laminate according to claim 1, wherein the cover layer shrinks insignificantly in comparison to the middle layer.

17. The laminate according to claim 14, wherein the first cover layer and the second cover layer form a hydrophilic gradient.

18. An absorbent hygiene article comprising a fluid absorption and distribution layer, wherein said layer comprises the laminate according to claim 1.

19. A laminate having a first cover layer, a middle layer made of non-intersecting filaments, and a second cover layer, the non-intersecting filaments having been shrunk to cause alignment in the Z direction of the entire laminate by way of undulation or other geometric alignment of the middle layer,
   wherein the middle layer further comprises parallel monofilaments made of a first thermoplastic, oriented lengthwise; and monofilaments made of a second thermoplastic being deposited above and/or below the filaments of the first thermoplastic; the second monofilaments being arranged such that at least two parallel filaments of the first thermoplastic, aligned in a linear orientation, are intersected and bonded.

20. The laminate according to claim 19, wherein the first monofilaments have a melting or softening point that is at least 30° higher than the melting point of the fabric.

21. The laminate according to claim 19, wherein the second monofilaments are deposited sinusoidally over the first monofilaments that are oriented lengthwise.

22. The laminate according to claim 19, wherein the second monofilaments have a bicomponent polymer structure, where at least one polymer component having a melting or softening point that is at least 30° higher than that of the monofilaments made of a first thermoplastic.

23. An absorbent hygiene article comprising a fluid absorption and distribution layer, wherein said layer comprises the laminate according to claim 19.

* * * * *